United States Patent  [19]
Gupta et al.

[11] Patent No.: US 6,292,683 B1
[45] Date of Patent: Sep. 18, 2001

[54] METHOD AND APPARATUS FOR TRACKING MOTION IN MR IMAGES

[75] Inventors: Sandeep Narendra Gupta, Baltimore, MD (US); Marshall Sussman; Graham Wright, both of Toronto (CA)

[73] Assignee: General Electric Company, Milwaukee, WI (US)

[*] Notice: Subject to any disclaimer, the term of this patent is extended or adjusted under 35 U.S.C. 154(b) by 0 days.

[21] Appl. No.: 09/313,910

[22] Filed: May 18, 1999

[51] Int. Cl.[7] ............................................. A61B 5/055
[52] U.S. Cl. ........................... 600/410; 324/307; 324/309
[58] Field of Search ........................... 324/307, 309, 324/306; 600/410, 416, 413

[56] References Cited

U.S. PATENT DOCUMENTS

| | | | | |
|---|---|---|---|---|
| 4,716,368 | * | 12/1987 | Haacke | 324/309 |
| 4,761,613 | * | 8/1988 | Hinks | 324/309 |
| 5,111,820 | * | 5/1992 | Axel et al. | 600/410 |
| 5,323,110 | * | 6/1994 | Fielden et al. | 324/309 |
| 5,545,993 | * | 8/1996 | Taguchi et al. | 324/309 |
| 5,797,396 | * | 8/1998 | Geiser et al. | 600/407 |
| 5,953,439 | * | 9/1999 | Ishihara et al. | 382/107 |
| 6,067,465 | * | 5/2000 | Foo et al. | 600/410 |
| 6,157,677 | * | 12/2000 | Martens et al. | 348/699 |

OTHER PUBLICATIONS

Bailes, D., et al., Respiratory Ordered Phase Encoding (ROPE): A Method for Reducing Respiratory Motion Artefacts in MR Imaging, *Journal of Computer Assisted Tomography*, 9, 835–838 (1985).

Ehmann, R., et al., Adaptive Technique for High–Definition MR Imaging of Moving Structures, *Radiology*, 173, 255–263 (1989).

Wang, Y., et al., Algorithims for Extracting Motion Information from Navigator Echoes, *Magnetic Resonance in Medicine*, 36, 117–123 (1996).

Danias, P., et al., Prospective Navigator Correction of Image Position for Coronary MR angiography, *Radiology*, 203, 733–736 (1997).

(List continued on next page.)

*Primary Examiner*—Brian L. Casler
(74) *Attorney, Agent, or Firm*—Timothy J. Ziolkowski; Christian G. Cabou; Phyllis Y. Price

(57) ABSTRACT

The present invention relates to magnetic resonance imaging (MRI) and includes a method and apparatus to track motion of anatomy or medical instruments, for example, between MR images. The invention includes acquiring a time series of MR images of a region of interest, where the region of interest contains the anatomy or structure that is prone to movement, and the MR images contain signal intensity variations. The invention includes identifying a local reference region in the region of interest of a reference image and acquired from the time series. The local reference region of the reference image is compared to that of the other MR images and a translational displacement is determined between the local reference region of the reference image and of another MR image. The translational displacement has signal intensity invariance and can accurately track anatomy motion or the movement of a medical instrument during an invasive procedure. The translational displacement can be used to align the images for automatic registration, such as in myocardial perfusion imaging, MR angiography, fMRI, or in any other procedure in which motion tracking is advantageous. Two implementations of the invention are disclosed, one in which a correlation coefficient is calculated and used to determine the translational displacement, and one in which the images are converted to a binary image by thresholding and after computation of a filtered cross-correlation, a signal peak is located and plotted as the translational displacement.

60 Claims, 4 Drawing Sheets

OTHER PUBLICATIONS

Hardy, C., et al., Robust Coronary MRI by Spiral Fluoroscopy with Adaptive Averaging, *ISMRM*, 22 (1998).

Butts, K., et al., Isotrophic Diffusion–Weighted and Spiral-navigated Interleaved EPI for Routine Imaging of Acute Stroke, *Magnetic Resonance in Medicine*, 38, 741–749 (1997).

Lee, C., et al., A Prospective Approach to Correct for Inter–Image Head Rotation in fMRI, *Magnetic Resonance in Medicine*, 39, 234–243 (1998).

Fayad, Z., et al., Right Ventricular Function Using MR Tagging: Normals Versus Chronic Pulmonary Hypertension, *Magnetic Resonance in Medicine* 39, 116–123 (1998).

McVeigh, E., et al., Imaging Asynchronous Mechanical Activation of the Paced Heart with Tagged MRI, *Magnetic Resonance in Medicine*, 39, 507–513 (1998).

McVeigh, E., et al., Improved Sampling of Myocardial Motion with Variable Separation Tagging, *Magnetic Resonance in Medicine*, 39, 657–661 (1998).

Unal, O., et al., A Rapid 2D Time–Resolved Variable–Rate k–Space Sampling MR Technique for Passive Catheter Tracking During Endovascular Procedures, *Magnetic Resonance in Medicine*, 40, 356–362 (1998).

Lewis, J.P., Fast Normalized Cross–Correlation, http://www.idiom.com/~zilla/Papers/nvisionInterface/nip.html, Nov. 6, 1998.

Taylor, J., An Introduction to Error Analysis, University Science Books, 1982, p. 248.

Kerr, A., et al., Realtime Interactive MRI on a Conventional Scanner, *Magnetic Resonance in Medicine*, 38, 355–367 (1997).

Wilke, N., et al., Concepts of Myocardial Perfusion Imaging in Magnetic Resonance Imaging, *Magnetic Resonance Quarterly*, vol. 10, No. 4, pp. 249–286 (1994).

van den Elsen, P., et al., Medical Image Matching—A Review with Classification, *IEEE Engineering in Medicine and Biology*, pp. 26–39 (1993).

Oppenheim A.V. et al., Discrete Time Signal Processing, Prentic Hall, N.J., pp. 63–67 (1989).

Lewis, J.P., Fast Template Matching, *Vision Interface '95*, p. 120–123 (1995).

\* cited by examiner

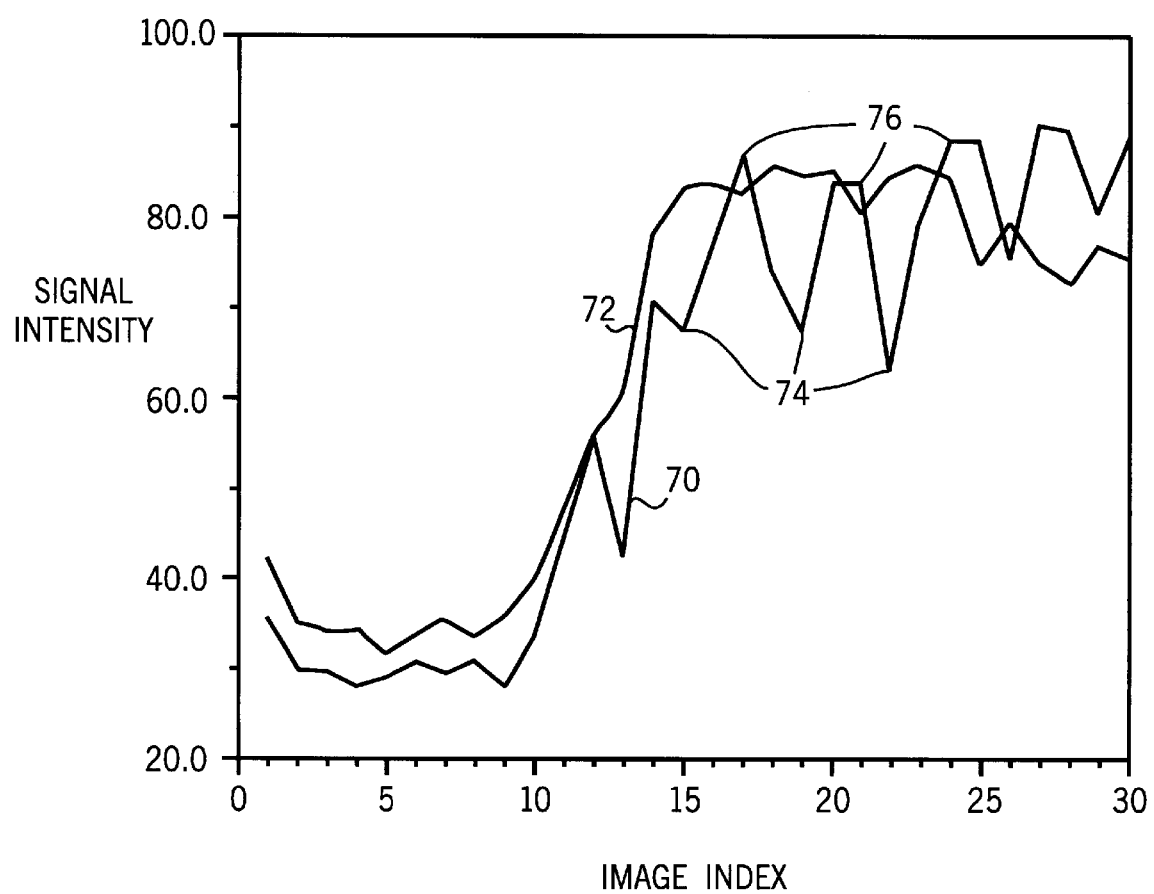

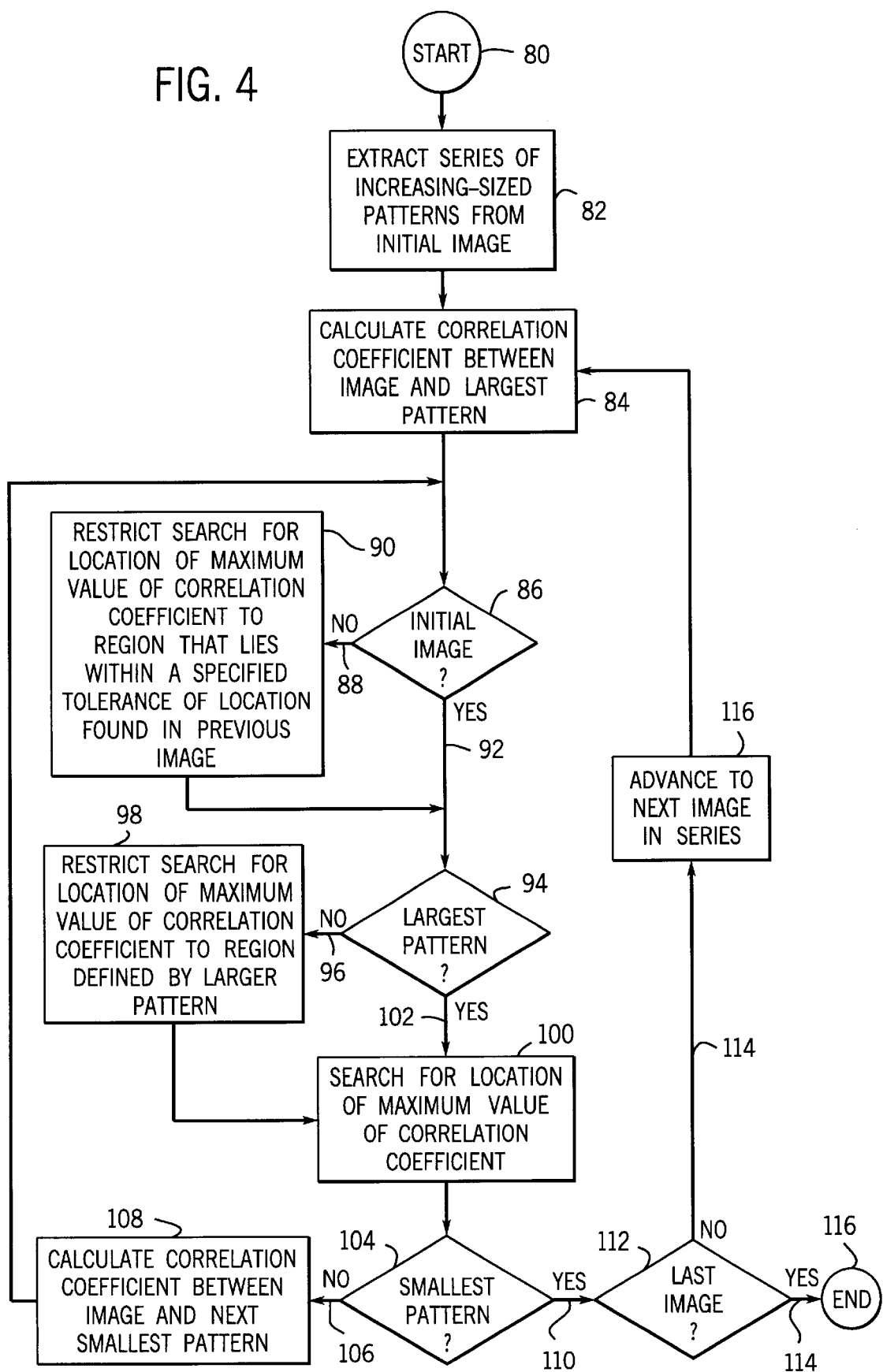

METHOD AND APPARATUS FOR TRACKING MOTION IN MR IMAGES

BACKGROUND OF THE INVENTION

The present invention relates generally to magnetic resonance imaging (MRI), and more particularly to a method and apparatus to track motion, such as anatomy movement, between MR images for efficient and effective MR image registration.

The ability to track motion in a time series of images is essential for a number of different MRI applications. For example, motion artifact suppression techniques require a measurement of motion upon which to take corrective action. Such motion artifact correction has been useful in a variety of applications, including coronary artery imaging such as an MR angiography (MRA), functional MR imaging (fMRI) such as to study brain function, and diffusion imaging. Another motion tracking application is the monitoring of heart wall motion which would be useful to assess the severity and extent of damage in ischemic heart disease. Another application for motion tracking is interventional imaging, such as monitoring the position of a scalpel or other instrument during an interventional procedure.

MR imaging of the coronary arteries, or MR angiography (MRA), has typically been performed using a technique to limit the MRI acquisition to avoid motion artifacts. Such techniques include requiring the patient to withhold breathing during the imaging, using oblique single-sliced image techniques, or respiratory-gated 3D imaging techniques. However, repeated breath holding may not be feasible for many coronary patients and navigation techniques to-date have not generally provided a robust method which works over a range of different breathing patterns in a variety of patients. Another drawback to these approaches is that success or failure is usually not apparent for some time after the start of imaging, and many times not until the imaging has been completed.

Another application requiring accurate compensation for anatomy movement includes myocardial perfusion imaging to detect the passage of a contrast agent through muscle tissue in the heart and to study the blood flow in the micro-circulation of the heart non-invasively. Typically, perfusion imaging consists of using injected contrast agents together with rapid imaging during the first pass with carefully optimized pulse-sequence parameters. Quantification of blood flow from these images is carried out with a region of interest based signal, time-intensity curve analysis. To avoid cardiac motion artifacts, the perfusion images are typically acquired with ECG gating. However, since the period of image acquisition is usually 1–2 minutes long, the images suffer from significant respiratory motion artifacts. This then requires a manual registration and analysis of the perfusion images which is cumbersome and time-consuming because the user must carefully arrange each image to compensate for the respiratory motion before proceeding to a region of interest time-intensity analysis.

The goal of myocardial perfusion imaging is to detect and characterize the abnormal distribution of myocardial blood flow. The ability to extract quantitative perfusion indices such as time-to-peak, contrast enhancement ratio, and the slope from first-pass contrast-enhanced MR images requires a generation of myocardial and blood-pool time-intensity curves for desired regions-of-interest. The computation of these curves is complicated when patients do not suspend respiration adequately, which then results in an image mis-registration over time. This mis-registration occurs frequently due to the fact that the breath-hold duration required to capture first-pass kinetics is typically 20–30 seconds. An accurate spatial alignment of images over a period of time is necessary for creating representative time-intensity curves. Therefore, it would be desirable to have an automatic registration system to track motion and provide automatic compensation for in-plane translation.

A prior art method of MR motion tracking that has had some success is a pattern matching technique. Under this method, an initial region, or pattern, containing the anatomy of interest is saved as a referenced region. In order to track motion occurring in a series of images, the pattern matching technique finds the location in each of the MR images that best matches the initial pattern. The difference between the various pattern matching techniques is the manner in which the best location is chosen. In MR, the previous techniques used for pattern matching have been a least squares technique and a cross-correlation technique. The least squares technique attempts to find a location $(\xi,\eta)$ in an image $f(x,y)$, that minimizes the squared distance $d^2$ between the image and the MxN pattern $h(x,y)$ given by:

$$d^2(\xi,\eta)=\Sigma_{i=1}^{M}\Sigma_{j=1}^{N}\{f(x_i-\xi,y_j-\eta)-h(x_i,y_j)\}^2 \quad (1)$$

$$=\Sigma_{i=1}^{M}\Sigma_{j=1}^{N}\{f(x_i-\xi,y_j-\eta)^2-2f(x_i-\xi,y_j-\eta)h(x_i,y_j)+h(x_i,y_j)^2\} \quad (2)$$

where $(x,y)$ and $(\xi,\eta)$ are position coordinates, $f(x,y)$ is the image, $h(x,y)$ is the pattern for matching, M and N are the x,y dimensions of the pattern, and i, j are the summation indices.

The cross-correlation technique is a derivative of the least squares technique and attempts to find the pattern match by maximizing the second term of Eqn. 2. The advantage of cross-correlation over least squares is that it can be calculated very rapidly by Fourier transform techniques. The cross-correlation technique has heretofore been the most widely used method of motion tracking and correction due to the rapid calculation time.

One disadvantage of the least squares and the cross-correlation techniques is that both fail to accurately match patterns in images where there is a local and/or global bias (v) or gain (u) in the image. That is, if $f(x,y)=uf_0(x,y)+v$, where $f_0$ is the initial image and f is the current image. An example of where such bias or gain variations can occur is in the aforementioned case of myocardial perfusion imaging where blood flow into and out of the image plane is expected and causes signal intensity variations. Under such conditions, the least squared and cross-correlation technique may not accurately match patterns.

As can be drawn from Eqn. 2, in order to accurately find the minimum distance between the image and the pattern, cross-correlation requires the additional assumption of constant energy in every MxN region of the image. In practice, however, such an assumption is often not satisfied. This problem is more acute in smaller patterns, such as a 16×16 pattern, than in larger images, such as in 32×32 pattern. As a result, cross-correlation has primarily been used in one-dimensional navigator echoes for the purpose of reducing motion artifacts. Such applications have been largely successful because the cross-correlation technique was used to detect gross motions of the whole anatomy. In these cases, the patterns to be matched were relatively large, and usually, a one-dimensional projection of the whole anatomy. However, for detecting more localized motion in two dimensional images, such as regions of the heart, coronary arteries, or surgical instruments, the cross-correlation technique is ineffective.

It would therefore be desirable to have a method and apparatus capable of accurately tracking motion between MR images that is independent of signal intensity variations, such as local bias, global bias, and/or gain within MR images and/or between MR images to allow either efficient tracking of the motion or for the sake of tracking motion or for using the motion tracking to compensate for motion between images by automatically aligning the images based on the motion tracking.

SUMMARY OF THE INVENTION

The present invention relates to a system and method to track movement in MR images that solves the aforementioned problems. In one application, an automatic image registration algorithm is proposed which greatly reduces the time required for analyzing MR studies and improves the accuracy of the signal intensity analysis. The automatic image registration system is particularly advantageous in myocardial perfusion imaging, coronary artery imaging, diffusion imaging, motion tracking as in fMRI, and medical instrument tracking in an interventional procedure.

Unlike the prior art least squares and cross-correlation techniques, the method and apparatus of the present invention is capable of tracking motion in a time series of MR images that can detect linear relationships between the images and is insensitive to signal intensity variations, such as bias and gain deviations that can occur between or within images.

A method of tracking motion between MR images is disclosed which includes acquiring a time series of MR images of a region of interest of a patient, where the region of interest contains structure, such as anatomy or an instrument, that is prone to movement and where the series of MR images is expected to contain signal intensity variations. The method includes identifying a local reference region in the region of interest of a reference image and compares the local reference region of the reference image to regions of equal size in another MR image. A translational displacement is determined between the local reference region of the reference image and another MR image. The translational displacement has signal intensity invariance and can be used to accurately track anatomy or instrument movement in the region of interest.

In accordance with another aspect of the invention, an MRI apparatus to track motion between MR images includes a magnetic resonance imaging (MRI) system having a plurality of gradient coils positioned about a bore of a magnet to impress a polarizing magnetic field and an RF transceiver system having an RF modulator controlled by a pulse control module to transmit RF signals to an RF coil assembly to acquire MR images. The MRI apparatus of the present invention also includes a computer programmed to periodically activate the MRI system to acquire a time series of MR images having signal intensity variations. Each of the MR images captures a region of interest of a patient that contains structure that is prone to movement. The computer is further programmed to identify a local reference region in the region of interest of a reference image and to determine a translational displacement of the local reference region as compared to another MR image to track movement in the region of interest occurring between MR image acquisitions. The translational displacement determined has a signal intensity invariance such that the translational displacement is determinable and capable of providing tracking data of the movement occurring between MR image acquisitions regardless of signal intensity variations within a given image and between MR images.

In accordance with yet another aspect of the invention, a computer system is disclosed for use with an MRI apparatus having a computer programmed from a computer readable storage medium having thereon a computer program programmed to acquire a time series of MR images of a region of interest of a patient, where the region of interest contains anatomy that is prone to movement and where the MR images are capable of having signal intensity variations. The computer is also programmed to identify a local reference region in the region of interest of a selected reference image from the series of MR images and compare the local reference region in the reference image to regions of substantially equal size in other MR images. The computer program is then designed to determine a translational displacement between a selected MR image and the reference image that is independent and unaffected by signal intensity variations such that the translational displacement can be used to track anatomy movement in the region of interest.

Although the present invention is described as a method and apparatus for tracking motion, one application of such motion tracking is automatic registration of regions in MR images. In a preferred embodiment, the computer is further programmed to apply the measure of translational displacement to shift the selected MR images into alignment with the reference image and align the MR images in the series of MR images for automatic registration and thereby correct or compensate for anatomy movement in the region of interest that occurs between MR image acquisitions.

The present invention discloses two ways to implement the aforementioned method and apparatus, both of which are independent of signal intensity variations. In one, each of the MR images is converted to a binary image using a thresholding technique after which, a cross-correlation image is created and the peak of the cross-correlation image is detected. A shift factor is computed from the peak location, after which the image can be shifted to align the image with a reference image. In another implementation, MR image patterns are matched based on a calculation of a correlation coefficient between an established pattern and regions in the MR images. The location that provides the largest correlation coefficient is chosen as the location of the pattern match. Unlike the least squares and cross-correlation techniques, the present technique using the correlation coefficient is insensitive to bias and gain variations. It is noted that the correlation coefficient can be calculated in a time comparable to cross-correlation, which is substantially faster than the least squared method. An additional benefit of calculating the correlation coefficient is that the value of the coefficient provides an indication of how closely the pattern resembles the matched region in the image.

Various other features, objects and advantages of the present invention will be made apparent from the following detailed description and the drawings.

BRIEF DESCRIPTION OF THE DRAWINGS

The drawings illustrate the best mode presently contemplated for carrying out the invention.

In the drawings:

FIG. 3 is a graphical representation having two time intensity curves of a region of interest, one acquired using the present invention and one without.

FIG. 4 is a flow chart of another embodiment of the present invention.

DETAILED DESCRIPTION OF THE PREFERRED EMBODIMENT

Figure 1:
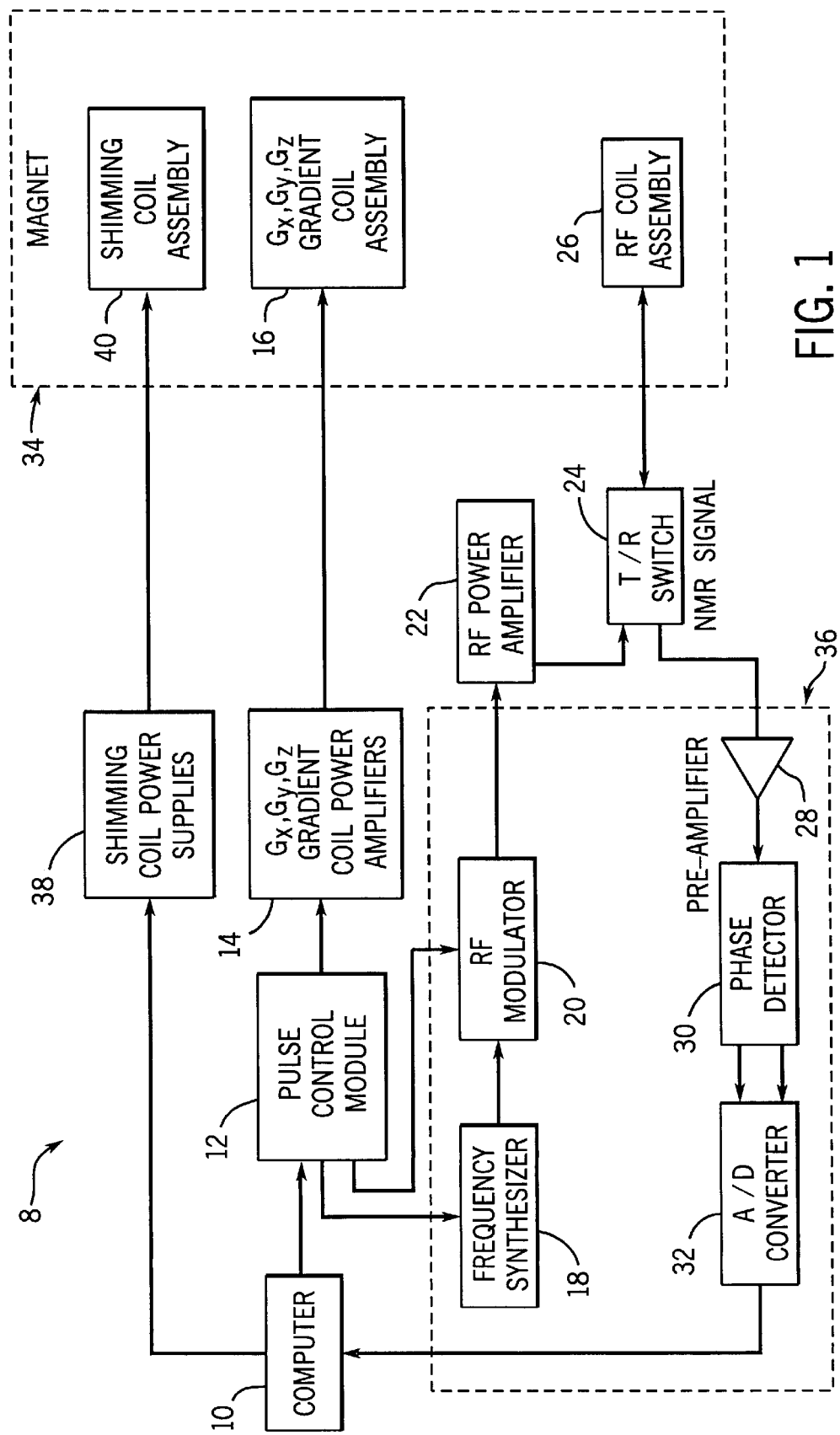
FIG. 1 is a schematic block diagram of an NMR imaging system for use with the present invention.

Referring to FIG. 1, a nuclear magnetic resonance (NMR) imaging system of a type suitable for the practice of the invention includes a computer 10 which controls gradient coil power amplifiers 14 through a pulse control module 12. The pulse control module 12 and the gradient amplifiers 14 together produce the proper gradient waveforms Gx, Gy, and Gz, for either a spin echo, a gradient recalled echo pulse sequence, a fast spin echo, or other type of pulse sequences. The gradient waveforms are connected to gradient coils 16 which are positioned around the bore of the magnet 34 so that gradients Gx, Gy, and Gz are impressed along their respective axes on the polarizing magnetic field Bo from magnet 34.

The pulse control module 12 also controls a radio frequency synthesizer 18 which is part of an RF transceiver system, portions of which are enclosed by dashed line block 36. The pulse control module 12 also controls an RF modulator 20 which modulates the output of the radio frequency synthesizer 18. The resultant RF signals, amplified by power amplifier 22 and applied to RF coil 26 through transmit/receive switch 24, are used to excite the nuclear spins of the imaged object (not shown).

The NMR signals from the excited nuclei of the imaged object are picked up by the RF coil 26 and presented to preamplifier 28 through transmit/receive switch 24, to be amplified and then processed by a quadrature phase detector 30. The detected signals are digitized by a high speed A/D converter 32 and applied to computer 10 for processing to produce NMR images of the object. Computer 10 also controls shimming coil power supplies 38 to power shimming coil assembly 40.

The present invention includes a method and system for tracking motion between MR images acquired in a time series for use with the above-referenced MRI system, or any similar or equivalent system for obtaining MR images.

It is well known that motion between images acquired with MRI greatly reduces their utility and effectiveness. Prior art attempts at tracking motion using cross-correlation and other simple distance measurement techniques have not been effective where signal intensities vary either within images, between images, or both. Such signal variations arise regularly in MR imaging due to flow effects, motion effects, or wash-through of contrast agents, among other reasons. The present invention solves the aforementioned problems with a local pattern matching technique that is insensitive to signal variations in and between MR images. It is understood the term signal intensity variations includes variations over space and time, and includes pixel by pixel changes both within an image and changes between images.

Figure 2:
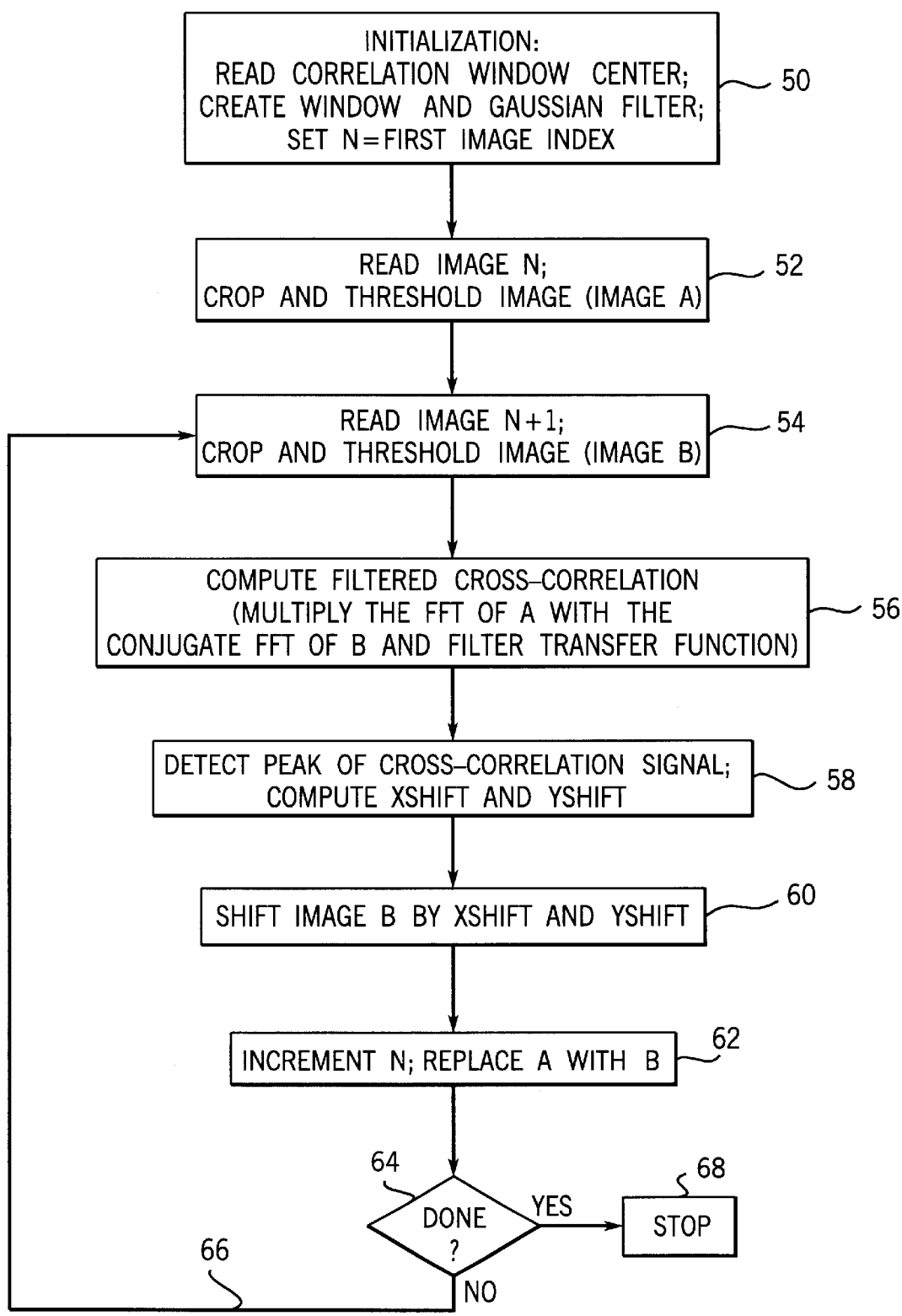
FIG. 2 is a flow chart of one embodiment of the present invention.

In one embodiment, as shown in FIG. 2, an iterative cross-correlation scheme is implemented in the Fourier domain on suitably processed input MR images that first includes an initialization step 50 during which a correlation window size is empirically determined based on the image pixel size. In a preferred embodiment for myocardial perfusion imaging, a correlation window is chosen sufficiently large enough to just encompass the entire heart of a subject patient. A 64×64 correlation window centered in the left ventricular chamber has been shown to work reliably. The correlation window size must be chosen based on the anatomy to be imaged and the image pixel size. If the window is initially selected too large, poor registration performance may be expected due to the motion of the chest wall, and if the window is chosen too small, poor registration can be attributed to inadequate structure information for the cross-correlation. A first image index N is initialized at 50 and the first image is read at 52, then the image is cropped to the desired correlation window size, and then converted to a binary image.

In a preferred embodiment, the conversion to a binary image is done with a thresholding technique in which an intensity threshold for each MR image is determined by first obtaining an average pixel intensity for each image. Then a binary 1 is assigned to all pixel values at or above the average pixel intensity and a binary 0 is assigned to all pixel values below the average pixel intensity. Depending on the application, it is apparent that these assignments may be reversed without departing from the spirit of the invention.

A second image is then read, cropped, and converted to a binary image at 54. A filtered cross-correlation of the two images is then calculated by implementing a convolution in the Fourier domain at 56. An example of such a calculation can be found in A. V. Oppenheim and R. W. Schafer, *Discrete-Time Signal Processing*, Prentice Hall International, 1989. The filter transfer function used is a centered Gaussian filter kernel with a window size of 128 pixels and a variance of 100.0 to filter each image.

A peak of the cross-correlation signal in the cross-correlation image is then located at 58 and a shift factor is calculated therefrom in an x-direction and in a y-direction. The second image is then shifted to align the second image with the first reference image at 60. Preferably, this procedure is repeated until a zero-shift is obtained. This pair of images is then considered registered. The index N is incremented at 62 and preferably, the first image is replaced with the shifted second image, and as long as there are images in the series to be aligned 64, 66, the aforementioned steps are repeated until all the MR images in the time acquired series of MR images are automatically registered 64, 67, at which time the automatic registration of the MR images is complete 68. The decision block 64 is based on the range of images to be registered as identified by the user.

This embodiment of the present invention has been tested and validated on nine patient volunteer studies in a cardiac MRI perfusion analysis implementation. FIG. 3 shows a graph of image index versus signal intensity having time-intensity curves of a region of interest showing unregistered images 70 and registered images 72. The sharp spikes 74 in the unregistered images graphs 70 indicates movement that was the result of respiratory motion. The peaks 76 result from blood inflow. The registered image curve 72 was acquired after being automatically registered according to the invention as shown and described with reference to FIG. 2. As indicated in FIG. 3, a significantly reduction in motion artifacts (misalignments) was observed in all studies. Of the 380 images studied in the unregistered images, 166 image pairs, or 43.7%, suffered from significant motion artifacts defined as motion larger than 2 pixels. After automatic registration, a mere 17 image pairs, or 4.4%, suffered from a significant, though greatly reduced, motion. The studies were conducted using a GE Signa™ 1.5T MRI system with a high performance gradient subsystem (40 mT/m, 150 T/m/sec). To quantify the performance of the algorithm, the motion of the right ventricular insertion point was measured for both the unregistered and registered images. The invention resulted in a ten-fold reduction in the number of images corrupted by misalignment.

Referring to FIG. 4, another implementation of the present invention is described in which a correlation coefficient is calculated and used for tracking motion. A pattern is defined and matched based on a calculation of the correlation coefficient between the pattern and regions in other MR images. The location of the best pattern match is based on the location which gives the largest correlation coefficient. A translational displacement is determined based on the location of the best pattern match. The correlation coefficient is based on a least squares distance function, as will be described in further detail hereinafter.

Referring to the flow chart of FIG. 4, after initialization and acquisition of a time series of MR images at 80, a series of patterns are extracted from an initial reference image at 82. This step is an optimizing step in which the smallest pattern having identifiable indicia is used for further matching. The system starts with a pattern which is likely to be too small for stability, then continues to increase the pattern size until a pattern having sufficient stability is found, that being the largest pattern extracted. The correlation coefficient is then calculated between the image and the largest pattern at 84, as will be described hereinafter. The algorithm starts with the largest pattern to maintain stability and then iterates down to the smallest pattern. After calculating the correlation coefficient between the image and the largest pattern at 84, the system checks to see if the image is the first image of the series 86, and if it is not 88, a search for the location for the maximum value of the correlation coefficient is restricted to a specified region of where the largest correlation coefficient was found in the previous image 90. Once that search is restricted, or if the image was the first image 86, 92, the system checks to see if it is still in the largest pattern mode 94. If it is not the largest pattern 96, the search for the maximum value of the correlation coefficient location is restricted to a region defined by the previous larger pattern 98, after which the location for the maximum value of the correlation coefficient is found in that pattern 100. Similarly, if a current pattern is the largest pattern 94, 102, the system searches for the location of the maximum correlation coefficient value at 100. If the algorithm has not reached the smallest pattern 104, 106, the correlation coefficient is calculated between the present image and the next smallest pattern at 108 and then returns to the initial image decision determination at 86. Once the smallest pattern is reached 104, 110 the system checks to see if the last image has been used to calculate the correlation coefficient at 112. If it is not the last image 112, 114, the next image in the series is loaded 116 and the correlation coefficient is again calculated at 84. When each pattern has been calculated 104, 110, for every image 112, 114, the motion tracking algorithm is complete 116.

The following discussion describes how the correlation coefficient is calculated. First, a definition of a distance function between the pattern and the region of the image that is being tested is described. A modified least squares distance function ($d'^2$) that is used is given by:

$$d'^2(\xi,\eta) = \Sigma_{i=1}^{M}\Sigma_{j=1}^{N}\{f'(x_i-\xi,y_j-\eta)-h'(x_i,y_j)\}^2;$$

$$f'(x,y) = [f(x,y)-\bar{f}_{(\xi,\eta)}]/\sigma_{f(\xi,\eta)}$$

$$h'(x,y) = [h(x,y)-\bar{h}]/\sigma_h \quad (3)$$

where $\bar{f}_{(\xi,\eta)}, \sigma_{f(\xi,\eta)}$ are the mean and standard deviation of $f(x,y)$ in the M×N region of the image centered at the location $(\xi,\eta)$ and $\bar{h}, \sigma_h$ are the mean and standard deviation of the pattern $h(x,y)$. $d'^2(\xi,\eta)$ can be simplified to yield:

$$d'^2(\xi,\eta) = 2 - 2\Sigma_{i=1}^{M}\Sigma_{j=1}^{N}f'(x_i-\xi,y_j-\eta)h'(x_i,y_j)$$

$$= 2 - 2\Sigma_{i=1}^{M}\Sigma_{j=1}^{N}[f(x_i-\xi,y_j-\eta)-\bar{f}_{(\xi,\eta)}][h(x_i,y_j)-\bar{h}]/[\sigma_{f(\xi,\eta)}\sigma_h]$$

$$= 2 - 2r(\xi,\eta) \quad (4)$$

where $r(\xi,\eta)$ is the correlation coefficient between the image and the pattern at the location $(\xi,\eta)$. The preferred pattern match is defined as one which maximizes the correlation coefficient. The value of the correlation coefficient provides an indication of the similarity of the pattern in the reference image with regions in another MR image. As the image and pattern approach a perfect linear relationship, the correlation coefficient approaches unity.

Preferably, the numerator and denominator in Eqn. 4 are calculated separately in order to optimize computer time and provide a rapid result. The numerator of the correlation coefficient, known as the covariance, is given by:

$$\Sigma_{i=1}^{M}\Sigma_{j=1}^{N}[f(x_i-\xi,y_j-\eta)-\bar{f}_{(\xi,\eta)}][h(x_i,y_j)-\bar{h}]$$

$$= \Sigma_{i=1}^{M}\Sigma_{j=1}^{N}f(x_i-\xi,y_j-\eta)[h(x_i,y_j)-\bar{h}]. \quad (5)$$

Eqn. 5 is a simple convolution that can be calculated rapidly in the Fourier domain. The denominator of the correlation coefficient ($[\sigma_{f(\xi,\eta)}\sigma_h]$) can be calculated rapidly in the image domain by a running sum technique as disclosed in J. P. Lewis, *Fast Template Matching*, Vision Interface '95, pg. 120–123, 1995; J. P. Lewis, *Fast Normalized Cross-Correlation*, http://www.idiom.com/~zilla/Papers/nvisionInterface/nip.html, Nov. 6, 1998.

In order to track motion of a non-rigid body using the correlation coefficient, it is desirable to have a method to determine how accurately the motion is being tracked. That is, it is preferable to have some criterion upon which to accept or reject the pattern match. One approach to resolving this problem is to analyze the value of the correlation coefficient obtained for each pattern match. The probability P of obtaining a value of the correlation coefficient r greater than $r_0$ is given by:

$$P(r \geq r_0) = [1/\sqrt{\pi}]\Gamma[(M \cdot N-1)/2]\Gamma[(M \cdot N-2)/2]\int_{r_0}^{1}(1-r^2)^{(M \cdot N-4)/2}dr \quad (6)$$

where $\Gamma$ is the commonly known probability gamma function. Based on Eqn. 6 for a specified confidence level, the threshold $r_0$ can be set such that any values of the correlation coefficient r that fall below $r_0$ can be rejected.

Another method for accepting/rejecting matches is based on a time series analysis of the motion. That is, a translational displacement determination can be accepted or rejected based upon a comparison of a translational displacement parameter to a given tolerance. For example, a predetermined tolerance can be set for total maximum displacement, velocity, or acceleration, and any value above or below a specific tolerance can be rejected.

As previously mentioned, when tracking motion of a non-rigid body, the smaller the pattern size, the more accurate the motion tracking because there is less deformation over a smaller sized region. However, the smaller the pattern size, the less stable the motion tracking algorithm becomes because with smaller patterns, it is more likely that there will be multiple locations in the image that are similar to the pattern. To improve the stability of the pattern match, the search region can be restricted based on a specified displacement, velocity, or acceleration tolerance. In this manner, the number of locations similar to the pattern that are searched by the algorithm can be reduced.

Accordingly, the present invention includes a method of tracking motion as between MR images having the steps of acquiring a time series of MR images of a region of interest of a patient, where the region of interest contains structure that is prone to movement and where the series of MR images contains signal intensity variations. The structure may be anatomy, a medical instrument, or any other moving object. The method also includes identifying a local reference region in the region of interest of a reference image from the series of MR images and comparing the local reference region of the reference image to other MR images in the series of MR images. The invention also includes determining a translational displacement between the local reference region of the reference image and another image. The translational displacement has a signal intensity invariance to accurately track structure movement in the region of interest.

The invention also includes an MRI apparatus to track structure movement between MR images that includes an MRI system having a plurality of gradient coils positioned about a bore of a magnet to impress a polarizing magnetic field and an RF transceiver system, including an RF modulator controlled by a pulse control module to transmit RF signals to an RF coil assembly to acquire MR images. The MRI apparatus includes a computer program to periodically activate the MRI system and acquire a time series of MR images having signal intensity variations. The MR images acquired have a region of interest of a patient containing structure that is prone to movement. The computer also identifies a local reference region in the region of interest of a reference image from the series of MR images and in each MR image. The computer is also programmed to determine a translational displacement of the local reference region in the reference image as compared to that of another MR image to track movement of the structure in the region of interest that occurs between MR image acquisitions. The translational displacement has signal intensity invariance such that the translational displacement is determinable and capable of providing data for tracking structure movement occurring between MR image acquisitions regardless of signal intensity variations within a given MR image and/or between MR images.

The present invention also includes a computer system for use with an MRI apparatus comprising a computer programmed from a computer readable storage medium having thereon a computer program programmed to acquire a time series of MR images of a region of interest of a patient. The region of interest contains structure prone to movement and the MR images are capable of containing signal intensity variations. The program is designed to identify a local reference region in the region of interest for each MRI image and select a reference image from the series of MR images. The program compares the local reference region in the reference image to that of other images and determines a translational displacement between a selected MR image and the reference image that is independent and unaffected by the signal intensity variations such that the translational displacement can be used to track movement in the region of interest.

In a preferred embodiment, the computer is further programmed to apply the measure of translational displacement to shift the selected MR image into alignment with the reference image and align the MR images in the series of MR images for automatic registration and thereby correct for anatomy movement in the region of interest. Similarly, the system can be used to simply track motion of either the anatomy itself or of a medical instrument during an invasive procedure.

The present invention has been described in terms of the preferred embodiment, and it is recognized that equivalents, alternatives, and modifications, aside from those expressly stated, are possible and within the scope of the appending claims.

What is claimed is:

1. A method of tracking motion in a series of MR images comprising the steps of:

acquiring a time series of MR images of a region of interest of a patient, where the region of interest contains structure that is prone to movement during imaging and where the series of MR images contain signal intensity variations;

identifying a local reference region in the region of interest of a reference image from the series of MR images;

comparing the local reference region of the reference image to that of another MR image in the series of MR images; and determining a translational displacement between the local reference region of the reference image and another MR image, the translational displacement having a signal intensity invariance to accurately track structure movement in the region of interest.

2. The method of claim 1 further comprising the step of repeating the comparing and determining steps for each MR image acquisition until a steady state estimate of translational displacement is determined.

3. The method of claim 1 wherein the structure is anatomy and the method further comprises the step of applying the translational displacement to align the MR images of the anatomy in the series of MR images for automatic registration, thereby compensating for anatomy movement between MR images.

4. The method of claim 1 wherein the region of interest contains a patient's cardiac system and wherein the method includes the step of correcting MR image displacement due to respiratory movement to accomplish automatic image registration for cardiac MRI perfusion analysis.

5. The method of claim 1 wherein the step of determining a translational displacement includes converting each MR image to a binary image.

6. The method of claim 5 further comprising the steps of creating a cross-correlation image from the binary images of a previous MR image and a subsequent MR image and locating a peak of the cross-correlation image.

7. The method of claim 6 further comprising the step of computing a shift factor in an x-direction and in a y-direction from the cross-correlation image peak.

8. The method of claim 7 further comprising the step of shifting the subsequent MR image by the shift factor to align the subsequent MR image with the previous MR images.

9. The method of claim 8 further comprising the step of repeating the steps of creating a cross-correlation image, locating a peak of the cross-correlation image, computing a shift factor, and shifting the subsequent MR image for each MR image in the series of MR images such that all the MR images in the series of MR images are automatically registered.

10. The method of claim 8 further comprising the step of repeating the steps of creating a cross-correlation image, locating a peak of the cross-correlation image, and computing a shift factor until the shift factor is equal to zero as between the previous MR image and the subsequent MR image.

11. The method of claim 5 wherein the step of converting each MR image to a binary image is further defined as determining an intensity threshold for each MR image.

12. The method of claim 11 wherein the step of determining an intensity threshold is further defined as obtaining an average pixel intensity for each image, and assigning a binary 1 to all pixel values above the average pixel intensity, and assigning a binary 0 to all pixel values below the average pixel intensity.

13. The method of claim 1 further comprising the step of calculating a correlation coefficient between each MR image and the reference image at a selected location and determining the translational displacement based on the correlation coefficient.

14. The method of claim 13 wherein the step of calculating a correlation coefficient is based on a least squares distance function.

15. The method of claim 13 further comprising the step of selecting a location having a largest correlation coefficient value across regions in an MR image.

16. The method of claim 15 further comprising the step of restricting the selection of a location based on a tolerance defined by the location and size of a previously selected larger pattern, at a location where the correlation coefficient is maximum.

17. The method of claim 13 wherein the correlation coefficient provides an indication of similarity of a selected region of the reference image with that of another MR image.

18. The method of claim 13 further comprising the step of aligning a selected image with the reference image based on the correlation coefficient calculated.

19. The method of claim 13 further comprising the steps of determining an accuracy of the translational displacement determined and rejecting the translational displacement on the accuracy determined.

20. The method of claim 19 wherein the step of determining an accuracy of the translational displacement includes analyzing the correlation coefficient against a probability of obtaining a value of the correlation coefficient that is greater than a threshold value $r_0$ and the step of rejecting the translational displacement is further defined as rejecting the translational displacement where the value of the correlation coefficient is less than the threshold value $r_0$.

21. The method of claim 19 wherein the step of determining an accuracy of the translational displacement includes a time series analysis of a movement parameter and the step of rejecting the translational displacement is based on whether the movement parameter exceeds a given tolerance.

22. The method of claim 1 wherein the region of interest is a patient's coronary artery and wherein the method includes the step of correcting MR image displacement to accomplish automatic image registration for MR angiography.

23. The method of claim 1 wherein the structure is a medical instrument and further comprises the step of tracking movement of the medical instrument during an invasive procedure.

24. An MRI apparatus to track structure movement in a series of MR images comprising:
a magnetic resonance imaging (MRI) system having a plurality of gradient coils positioned about a bore of a magnet to impress a polarizing magnetic field and an RF transceiver system having an RF modulator controlled by a pulse control module to transmit RF signals to an RF coil assembly to acquire MR images; and
a computer programmed to:
periodically activate the MRI system and acquire a time series of MR images having signal intensity variations, each MR image acquiring a region of interest of a patient containing structure that is prone to movement;
identify a local reference region in the region of interest of a reference image from the series of MR images; and
determine a translational displacement of the local reference region in the reference image as compared to another MR image to track structure movement in the region of interest occurring between MR image acquisitions, the translational displacement having signal intensity invariance such that the translational displacement is determinable and capable of providing tracking data of the structure movement occurring between MR image acquisitions regardless of signal intensity variations within a given MR image and between MR images.

25. The MRI apparatus of claim 24 wherein the structure is patient anatomy and the computer is further programmed to apply the translational displacement to align the MR images in the series of MR images to compensate for anatomy movement and accomplish automatic registration.

26. The MRI apparatus of claim 24 wherein the computer is further programmed to determine the translational displacement by converting a displaced MR image to a black and white binary image.

27. The MRI apparatus of claim 26 wherein the computer is further programmed to create a cross-correlation image from the black and white binary image and the reference image, and locate a peak of the cross-correlation image.

28. The MRI apparatus of claim 27 wherein the computer is further programmed to:
compute a shift factor in an x-direction and in a y-direction from the cross-correlation image peak; and
shift the displaced MR image by the shift factor to align the displaced MR image with the reference images.

29. The MRI apparatus of claim 26 wherein the computer is further programmed to:
determine an intensity threshold for each MR image by calculating an average pixel intensity for each image;
assign a binary 1 to all pixel values above the average pixel intensity; and
assign a binary 0 to all pixel values below the average pixel intensity.

30. The MRI apparatus of claim 24 wherein the computer is further programmed to continuously repeat the translational displacement determination for each MR image acquisition until a steady state estimate of translational displacement is determined.

31. The MRI apparatus of claim 24 wherein the computer is further programmed to calculate a correlation coefficient between each image from the series of MR images and the reference image at a selected location and determine the translational displacement based on the correlation coefficient.

32. The MRI apparatus of claim 31 wherein the computer is further programmed to separately calculate a numerator and a denominator of the correlation coefficient to efficiently calculate the translational displacement.

33. The MRI apparatus of claim 31 wherein the computer is further programmed to determine the translational displacement by calculating a least squared distance between the reference image and another MR image from the series of MR images.

34. The MRI apparatus of claim 31 wherein the computer is further programmed to select a location of a pattern match based on identifying a location having a maximum correlation coefficient value across an MR image.

35. The MRI apparatus of claim 31 wherein the computer is further programmed to provide an indication of location similarity between MR images based on the value of the correlation coefficient.

36. The MRI apparatus of claim 31 wherein the computer is further programmed to align a selected image with the reference image based on the correlation coefficient calculated.

37. The MRI apparatus of claim 31 wherein the computer is further programmed to reject any translational displacement determination based upon a probability of obtaining a correlation coefficient value that is less than a predetermined threshold value.

38. The MRI apparatus of claim 31 wherein the computer is further programmed to reject any translational displacement determination based upon a comparison of a translational displacement parameter to a given tolerance, the translational displacement parameter being one of: a total maximum displacement parameter, a velocity parameter, and an acceleration parameter, each a parameter of the structure movement in the region of interest.

39. A computer system for use with an MRI apparatus comprising a computer programmed from a computer readable storage medium having thereon a computer program programmed to:
    acquire a time series of MR images of a region of interest of a patient, where the region of interest contains structure that is prone to movement and where the MR images are capable of having signal intensity variations;
    select a reference image from the series of MR images;
    identify a local reference region in the region of interest for the reference image from the series of MR images;
    compare the local reference region in the reference image to other MR images in the series of MR images; and
    determine a translational displacement between a selected MR image and the reference image that is independent and unaffected by the signal intensity variations such that the translational displacement can be used to track movement of the structure in the region of interest between MR images.

40. The computerized system of claim 39 wherein the computer is further programmed to repeat the translational displacement determination between a next selected MR image and a previous MR image for each MR image acquisition until a steady state estimate of translational displacement is determined and each MR image in the series of MR images have the region of interest in alignment.

41. The computerized system of claim 39 wherein the structure is anatomy and the computer is further programmed to apply the measure of translational displacement to shift the selected MR image into alignment with the reference image and align the MR images in the series of MR images for automatic registration and thereby correct for anatomy movement in the region of interest.

42. The computerized system of claim 39 wherein the region of interest includes at least a portion of a heart and the computer is further programmed to correct MR image displacement due to respiratory movement of the heart to accomplish automatic image registration for cardiac MRI perfusion analysis.

43. The computerized system of claim 39 wherein the computer is further programmed to convert each MR image to a binary image to determine a translational displacement.

44. The computerized system of claim 43 wherein the computer is further programmed to create a cross-correlation image from the binary images of a previous MR image and from a subsequent MR image, and to locate a peak of the cross-correlation image.

45. The computerized system of claim 44 wherein the computer is further programmed to compute a shift factor in an x-direction and in a y-direction from the cross-correlation image peak.

46. The computerized system of claim 45 wherein the computer is further programmed to shift the subsequent MR image by the shift factor to align the subsequent MR image with the previous MR image.

47. The computerized system of claim 46 wherein the computer is further programmed to continuously repeat the creation of a cross-correlation image, locating a peak of the cross-correlation image, computing a shift factor, and shifting the subsequent image for each MR image in the series of MR images such that all the MR images in the series of MR images are automatically registered.

48. The computerized system of claim 46 wherein the computer is further programmed to continuously repeat the steps of creating a cross-correlation image, locating a peak of the cross-correlation image, and computing a shift factor between a given MR image and a given reference image until the shift factor is equal to zero.

49. The computerized system of claim 43 wherein the computer is further programmed to determine an intensity threshold for each MR image by converting each MR image to a binary image.

50. The computerized system of claim 49 wherein the computer is further programmed to obtain an average pixel intensity for each image, assign a binary 1 to all pixel values at and above the average pixel interest, and to assign a binary 0 to all pixel values below the average pixel intensity.

51. The computerized system of claim 39 wherein the computer is further programmed to calculate a correlation coefficient between each MR image and the reference image at a selected location and determine the translational displacement based on the correlation coefficient.

52. The computerized system of claim 51 wherein the computer is further programmed to calculate a correlation coefficient based on a least squares distance function.

53. The computerized system of claim 51 wherein the computer is further programmed to select a location for a pattern match based on identifying the correlation coefficient having a largest correlation coefficient value across an MR image.

54. The computerized system of claim 53 wherein the computer is further programmed to restrict a location search based on a tolerance defined by the location and size of a previously selected larger pattern, at a location where the correlation coefficient is maximum.

55. The computerized system of claim 51 wherein the computer is further programmed to provide an indication of similarity of location of the reference image with that of another MR image.

56. The computerized system of claim 51 wherein the computer is further programmed to align a selected image with the reference image based on the correlation coefficient calculated.

57. The computerized system of claim 51 wherein the computer is further programmed to determine an accuracy of the translational displacement determined, and accept the translational displacement based on the accuracy determined.

58. The computerized system of claim 57 wherein the computer is further programmed to analyze the correlation coefficient against a probability of obtaining a value of the correlation coefficient that is greater than a threshold value $r_0$ and reject a value of the translational displacement that is less than the threshold value $r_0$.

59. The computerized system of claim 51 wherein the computer is further programmed to determine an accuracy of the translational displacement that includes a time series analysis of an anatomy movement parameter and to reject any translational displacement that exceeds a given tolerance of the anatomy movement parameter.

60. The computerized system of claim 39 wherein the computer is further programmed to track movement of a medical instrument during an invasive procedure.

* * * * *